United States Patent [19]

Lim et al.

[11] Patent Number: 4,582,995
[45] Date of Patent: Apr. 15, 1986

[54] SPATIAL REGISTRATION CORRECTION FOR ROTATIONAL GAMMA CAMERAS

[75] Inventors: Chun B. Lim, Solon; Richard L. Chaney, Cuyahoga Falls; Roger J. Kump, Mentor, all of Ohio

[73] Assignee: Technicare Corporation, Solon, Ohio

[21] Appl. No.: 621,418

[22] Filed: Jun. 18, 1984

[51] Int. Cl.$^4$ ............................................. G01T 1/166
[52] U.S. Cl. ................................. 250/363 S; 250/369
[58] Field of Search ................. 250/363 S, 369, 252.1; 378/21, 196, 197

[56] References Cited

U.S. PATENT DOCUMENTS

| | | | |
|---|---|---|---|
| 4,216,381 | 8/1980 | Lange | 250/363 S |
| 4,426,578 | 1/1984 | Bradcovich et al. | 378/15 |
| 4,501,011 | 2/1985 | Hauck et al. | 378/150 |

OTHER PUBLICATIONS

Keyes, John W. Jr. "Computed Tomography in Nuclear Medicine", *Fundamentals of Digital Nuclear Medicine* by David Lieberman, Mosby, 1977, pp. 130–138.

*Primary Examiner*—Alfred E. Smith
*Assistant Examiner*—Carolyn E. Fields
*Attorney, Agent, or Firm*—Audley A. Ciamporcero, Jr.; Michael A. Kaufman

[57] ABSTRACT

A method for correcting predictable errors in the location of detected scintillation events acquired during emission computed tomography by a rotational scintillation gamma camera system. The method includes calibrating the rotational scintillation camera system and generating a look-up table comprising a set of pairs of x and y offset values, one pair for each viewing angle. The calibration reflects systemic deviations in the location of the rotating camera head detector measured in terms of x and y coordinates in the frame of reference of the detector for a plurality of view angles relative to the geometric ideal expected path. Once a look-up table is generated for a camera system, the detected location of each gamma event is altered in real time by adjusting in the camera head the x,y coordinate location of each event by the x,y offset values previously generated for the corresponding viewing angle associated with the detected event.

5 Claims, 7 Drawing Figures

| VIEW ANGLE | | $\Delta X(\theta)$ | $\Delta Y(\theta)$ |
|---|---|---|---|
| 1 | 0 DEG. | $\Delta X_1(0)$ | $\Delta Y_1(0)$ |
| 2 | 3 DEG. | $\Delta X_2(3)$ | $\Delta Y_2(3)$ |
| ⋮ | | | |
| i | $\theta$ DEG. | $\Delta X_i(\theta)$ | $\Delta Y_i(\theta)$ |
| N | | $\Delta X_N(\theta)$ | $\Delta Y_N(\theta)$ | ics have been proposed to perform three-dimensional imaging using an Anger type gamma camera. Since about 1980, several nuclear camera manufacturers have commercially introduced rotational type nuclear camera systems featuring a rotatable detector or camera head having a parallel hole collimator for data collection and an associated digital computer. The computer processes the collected data and performs known CT-type algorithms for reconstructing tomograms, i.e., two-dimensional images of a patient along a plane intersecting the patient.

SPATIAL REGISTRATION CORRECTION FOR ROTATIONAL GAMMA CAMERAS

TECHNICAL FIELD

This invention relates generally to scintillation or gamma cameras and in particular to a species of such cameras designed to rotate about a patient for emission computed axial tomography sometimes referred to as ECT or ECAT or SPECT, for single photon emission computed tomography.

BACKGROUND ART

Traditionally nuclear medicine focused on the generation of two-dimensional images constructed from a volume of interest, although a variety of imaging devices have been proposed to perform three-dimensional imaging using an Anger type gamma camera. Since about 1980, several nuclear camera manufacturers have commercially introduced rotational type nuclear camera systems featuring a rotatable detector or camera head having a parallel hole collimator for data collection and an associated digital computer. The computer processes the collected data and performs known CT-type algorithms for reconstructing tomograms, i.e., two-dimensional images of a patient along a plane intersecting the patient.

One such ECT system is described in U.S. Pat. No. 4,426,578 to Bradcovich, et al. and assigned to the assignee of the instant application. Bradcovich, et al. invented a system that features a counterbalanced C-arm supporting a camera head at one end thereof for rotation about a longitudinal axis through a patient. The radial distance between the camera head and the longitudinal axis is rendered adjustable by displacement of the C-arm along a circumferential path relative to a so-called carrier member which rotatably attaches the C-arm to a stationary base. Another ECT apparatus is described in U.S. Pat. No. 4,216,381 to Lange which features a rotatable detector head supported by a pair of elongated frame members that pivotally support the detector head as it rotates about a longitudinal axis through a patient. In the Lange arrangement, the radial distance between the longitudinal axis and the detector head is adjusted by tilting the elongated frame pair which are mounted within a circular frame supported, in turn, by a pair of upright stanchions.

Regardless of the type of apparatus used to support the rotatable camera head, the reconstruction algorithms are always based on the collection of projection data acquired at a set of viewing angles about the patient by the rotating detector and subsequent back-projection of the data by means of the computer. For a detailed discussion of the general approach see, for example, Keyes Jr., "Computed tomography in nuclear medicine". Accurate retracing of projection lines during back-projection is essential to assuring good image resolution and quality. In ECT operation a major degradation in image quality is caused by deviations between the actual photon paths of the data collected and their paths traced during back-projection.

Regardless of the specific type of reconstruction algorithm used to generate the desired planar images or tomograms, the techniques uniformly assume that the camera head always follows the expected path. In practice, however, the actual path of the detector deviates from the expected path so that its position at each angle will exhibit some offset due mostly to mechanical flex in the detector support system and, to a lesser degree, to electronic image plane shift. This is caused by slight variances among the camera's Photo Multiplier Tubes' operation which originates from the varying orientation between the detector plane and the earth/ambient magnetic field. These deviations have largely been ignored resulting in errors in the reconstructed image.

Errors of this sort are generally unavoidable. It has been found, however, that they are nonetheless predictable since the amount of deviation in any particular system is measurable. While the amount of deviation varies as a function of viewing angle the errors tend to be relatively constant from rotation to rotation over a long period of time.

SUMMARY OF THE INVENTION We have invented a method of correcting for deviations in the actual detector position of a rotating gamma camera from the expected position at each angle of rotation by having the location of each gamma event shifted by a known offset amount in the x,y directions at each viewing angle on an event-by-event basis. The application of the method involves the calibration of a gamma camera which includes generating a set of pairs of value for a plurality of viewing angles, each pair including an x and y offset value and altering, in real time, the detected location of each event by the appropriate offset values previously measured for the corresponding viewing angle.

DETAILED DESCRIPTION

Figure 1:
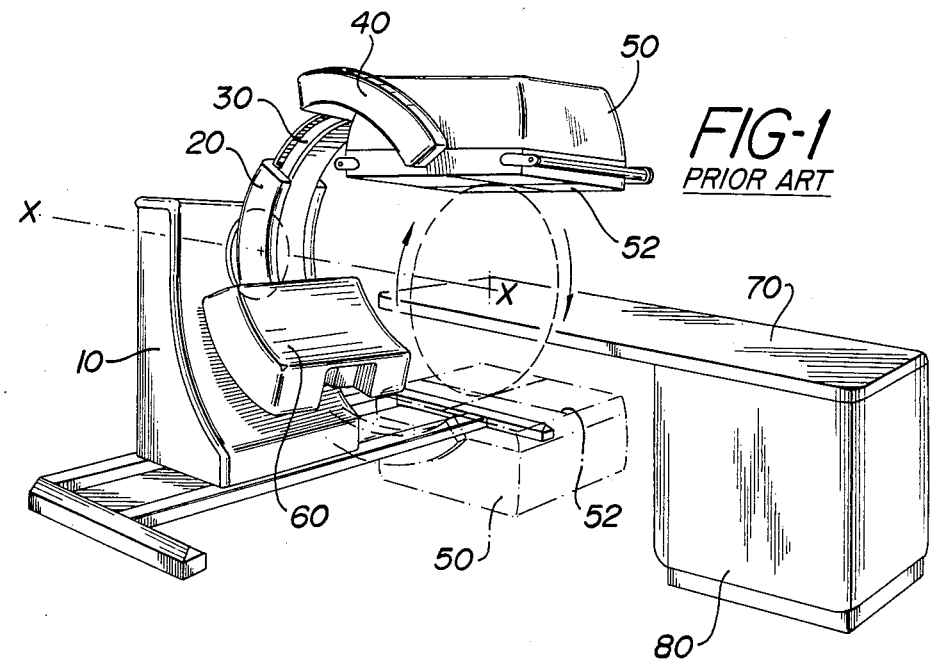
FIG. 1 is a diagrammatic perspective view of a prior art ECT apparatus featuring a rotatable camera head supported by a movable counterbalanced C-arm which provides for adjustment of the radius of rotation.

The apparatus illustrated in FIG. 1 is a prior ECT nuclear camera system commercially available under the name Omega 500 from Technicare Corporation, Solon, Ohio 44139. A detailed description of the Omega 500 is included in the '578 patent to Bradcovich, et al., the specification of which is incorporated herein by reference. Briefly, the nuclear camera comprises a base member 10 which is retained stationary for tomographic studies. Attached to base member 10 is carrier member 20 which is rotatable about a longitudinal axis x. Carrier member 20 is provided with a wide central groove for engaging a counterbalanced C-shaped support member or C-arm 30. One end of the C-arm 30 terminates in a yoke 40 to which a scintillation detector or camera head 50 is pivotally attached. To the other end of C-arm 30 is attached a counterweight 60. The patient being diagnosed is placed on a cantilevered patient support 70 which is secured to patient table 80. In operation, scintillation detector 50 is placed as close to the patient as possible while permitting clearance between the detector and the patient and the patient support during rotation of the camera and rotated about the patient along a defined path, generally circular. Data is acquired at a plurality of viewing angles or continuously as the camera head is rotated about the patient, typically by a motorized mechanism. The data collected from the various viewing angles is subsequently reconstructed by an associated digital computer (not shown) and tomographic images of desired planar slices of the patient are generated. The radius of rotation of the detector head is adjustable by moving the C-arm 30 relative to carrier member 20.

Figure 2:
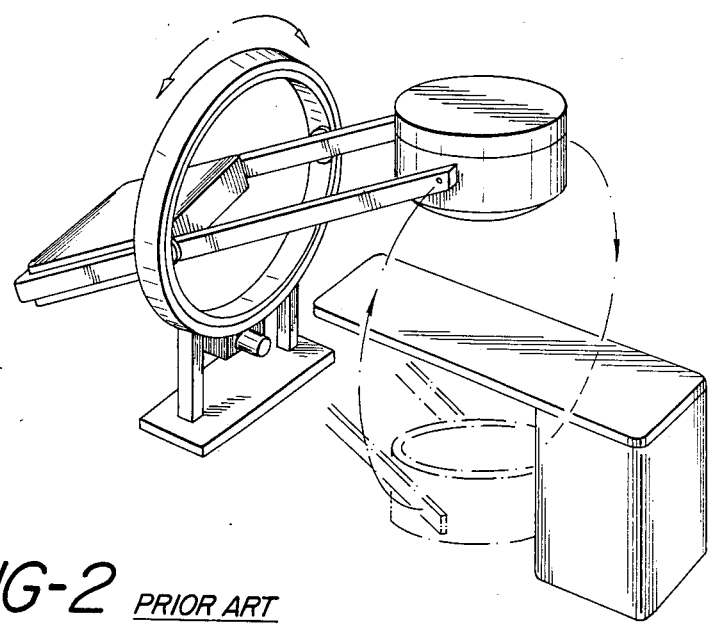
FIG. 2 is a diagrammatic perspective view of another prior art ECT apparatus featuring a rotatable camera head supported by a pair of elongated frame members tiltably mounted within a circular frame wherein the degree of tilt of said frame member defines the radial distance between the camera head and the axis of rotation.

Another example of a prior art ECT nuclear camera is shown in FIG. 2. Although the principles of the invention are equally applicable to a system such as illustrated in FIG. 2, the following description will be with reference to the system of FIG. 1. In the system shown in FIG. 1, the detector head 50 is an Anger camera which includes a rectangular sodium iodide crystal 52 which defines a large planar rectangular viewing face. Located behind the crystal 52 within the camera head 50 is a glass window and an arrangement of 55 PMTs. In operation, the camera head 50 is rotated about a patient such that the midpoint of planar face 52 defines a generally circular path. In this manner, the planar detector face 52, as illustrated diagrammatically in FIG. 3, collects data, i.e., detects gamma events, at viewing angles all around the object being examined. Since there are very substantial masses involved in the rotation of the gamma camera head 50, the support structure, particularly C-arm 30, flexes by varying amounts as the carrier member 20 is rotated about the x axis. As this flexing occurs, the path traversed by the planar face 52 deviates from the purely cylindrical path represented by the phantom circles C in FIG. 3.

Figure 3:
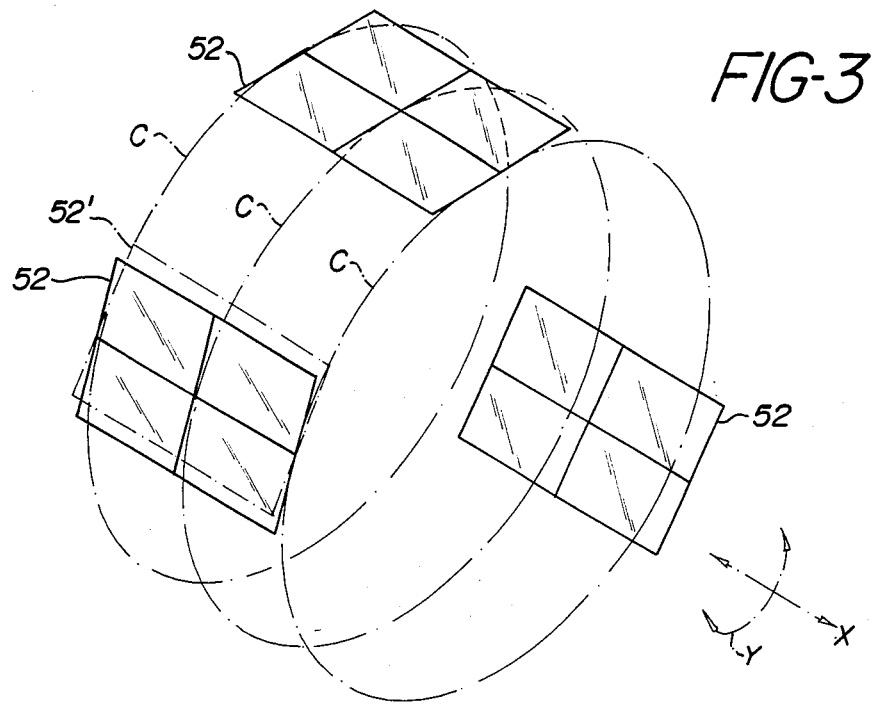
FIG. 3 is a diagrammatic geometric illustration showing, in phantom, an ideal cylindrical path of the planar face of the detector head of FIG. 1 and also showing deviations in both the x and y directions of the location of the face of said detector head at three angular locations.

Using the hypothetical convention of 0° representing the twelve o'clock position, FIG. 3 shows the planar face 52 at the twelve o'clock position ideally situated. However, at the four o'clock position, or at approximately 120°, planar face 52 is shown to be offset by an increment along the direction of the longitudinal axis x. Thus, it can be seen, that when the data collected in the four o'clock position is combined with the data collected at the twelve o'clock position, a blurring error will be introduced since projections of the two sets of data will not be in registration. Similarly, FIG. 3 shows planar face 52 in the eight o'clock position, or at approximately 240°, exhibiting no deviation in the axial direction but being offset somewhat from the rotational axis or the y direction since the planar face should be located where indicated by phantom rectangle 52'.

Figure 4:
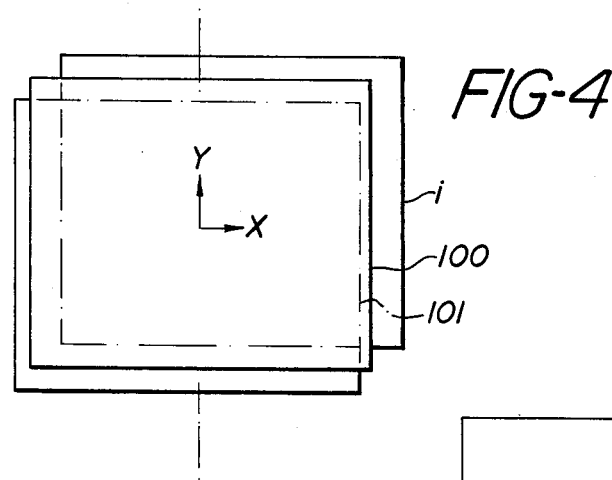
FIG. 4 is a diagrammatic representation of a set of planar images illustrating the lack of registration introduced by deviations in the location of the detector head relative to an assumed path, such as illustrated in FIG. 3.
Figure 5:
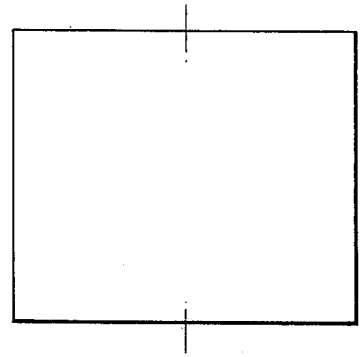
FIG. 5 is a diagram similar to FIG. 4 illustrating projections of data in registration.

Planar face 52 will, for any given viewing angle, have an offset in either or both the x and y directions in the frame of reference of the detector plane. Thus, for example, as shown in FIG. 4, a hypothetical frame designated 100 taken at zero degrees is properly aligned while frame 101 taken at one degree will have a deviation or offset in the x direction an amount $\Delta x_i$ and an offset in the y direction of $\Delta y_i$. In general, for a frame i taken at angle $\theta_i$ the offset will be $\Delta x_i$ in the x direction and $\Delta y_i$ in the y direction. Thus, as can be visually appreciated by the diagrammatic illustration of FIG. 4, the projection data collected from a set of viewing angles will not be in registry and, hence, errors will be introduced into the reconstructed image. Ideally, all of the projection data sets from the set of viewing angles should appear aligned, as illustrated in FIG. 5.

Thus, in order to retrace the photon path accurately during back-projection, each coordinate (x,y) of an event collected in the frame of reference of the detector should be converted to an (x',y') coordinate in the frame of reference of the projection data in accordance with the following relationship:

$$x' = x + \Delta x(\theta)$$

$$y' = y + \Delta y(\theta)$$

wherein $\Delta x(\theta)$ represents the offset in the x direction for viewing angle $\theta$ and $\Delta y(\theta)$ represents the offset in the y direction for that same viewing angle $\theta$.

Figures 6, 7:
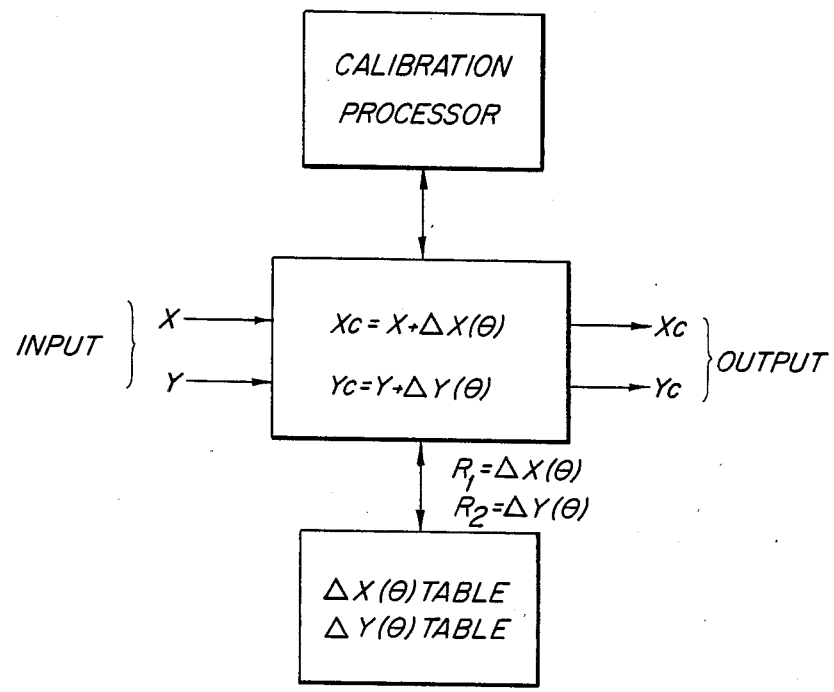
FIG. 6 is a diagrammatic flow chart of the correction method in accordance with the present invention.
FIG. 7 is an illustration of a look-up table generated during the calibration phase of the method outlined in FIG. 6.

In actual operation, a look-up table, such as illustrated in FIG. 7, is first generated for each particular machine representing its systemic path deviations. An example of the method for generating these calibration values will be given below, although the particular method should be governed by ease and convenience depending on the particular system being utilized. Once the calibration values are generated, they are stored in a storage memory area. Then, at each angle $\theta$, prior to the data collection, the matching pair of $x(\theta)$, $y(\theta)$ offsets are retrieved from the memory and stored in two registers $R_1$ and $R_2$.

If the number of viewing angles used turns out to be greater than the number of offset pair entries generated for the look-up table, the offset pair for each such intermediate viewing angle is interpolated from the available values in the look-up table. Then, during the data collection, each incoming event location detected on the detector face 52 by x and y coordinates is digitally converted in real time within the camera to the projection coordinate (x',y') in accordance with the following relationship:

$$x' = x + R_1$$

$$y' = y + R_2$$

wherein $R_1$, as stated above, is the x offset for the angle $\theta$ of the detector at the time the event is detected and $R_2$ is the offset in the y direction for the same angle.

If the camera head rotation is intended to be circular, then the expected path of the center of the camera face 52 is defined by a fixed radius. However, to accommodate patients of different sizes the radius of rotation, in such ECT systems as the Omega 500, is operator selectable. A separate look-up table may be generated for selected radii. Also, it is often desirable for improved resolution to have the camera head traverse in a noncircular path to thereby continuously maintain a minimum distance between the camera and the photon emitting patient whose sectional periphery is generally more elliptical than circular. Each such prescribed path will have predictable errors throughout the set of data collecting viewing angles and, in general, a look-up table may be generated for each path. The number of such tables will be governed by the severity of the problem and the differences in the calculated coordinate shifts for a viewing angle from one selectable path to another.

CALIBRATION

The preferred method for generating the y offset values for each angle $\theta$ requires collecting the point spread functions, PSF, from a source located within the field of view at each viewing angle. In other words, the response of the system to a single point or impulse at each viewing angle $\theta$. In general, the PSF or impulse response function of a system is the resultant beam of finite width produced by the system in response to seeing a point impulse. Fortuitously, the centroids of the PSF set carries the detector coordinate shift information. If we assume that $(x_1,y_1)$ $(x_2,y_2)$ ... $(x_i,y_i)$ ... $(x_n,y_n)$ are the centroids at angles $\theta_1, \theta_2, \ldots \theta_i, \ldots \theta_n$, then the axial shift in the y direction is found by calculating the $y_i$ set average ($\overline{Y}$) and $y_i$ deviation from the average at each angle as follows:

$$\overline{Y} = \left( \sum_{i=1}^{N} y_i \right) /N, \text{ and } \Delta Y_i = \overline{Y} - y_i$$

The above calculation will ensure that all angle PSF centroids are located at $\overline{Y}$ such that $$y_i + \Delta y_i = y_i + \overline{Y} - y_i = \overline{Y}.$$

The shifts in the transverse or x direction at each angle can also be found from the point source centroid data $(x_1, x_2, \ldots x_n)$ at each angle $(\theta_1, \theta_2, \ldots \theta_n)$, based on the fact that for parallel beam imaging the expected source position variation with angle is sinusoidal with no flexing of the support structure. If the point source is located off the rotation axis the distance from the rotation axis at each angle in case of no flex is given by $$x_i^0 = S \cdot \cos\theta_i + u \cdot \sin\theta_i,$$

where s and u are the distances measured in a fixed orthogonal coordinate centered at the rotation axis in a transverse plane. Suppose the distances of the collected centroids measured from the profile midpoints are $x_i^1$. Then the x offsets are found by their deviations, $\Delta x_i$.

$$\Delta x_i = (s \cdot \cos\theta_i + u \cdot \sin\theta_i) - x_i^1$$

where s and u are found by taking the first harmonic components in the Fourier series of the $x_i^1(\theta)$ set, given by $$s = \frac{1}{\pi} \cdot \sum_i \times i \cdot \cos\theta_i \cdot \Delta\theta_i$$

$$u = \frac{1}{\pi} \cdot \sum_i \times i \cdot \sin\theta_i \cdot \Delta\theta_i$$

If, s, u are in slight error from the true values, its only effect on the parallel ray reconstruction is the image shift in s,u directions by the corresponding error amounts.

The above description of the preferred embodiment represents a purely digital approach to correcting the location of each scintillation on an event by event basis. Alternatively, all events collected at an angle $\theta$ can be shifted by the amount of the centroid shift calculated for that angle $\theta$ in both the x and y directions, as, for example, by the above described calibration techniques.

We claim:

1. A method for correcting predictable errors in the location of detected scintillation events acquired during emission computed tomography by a rotational scintillation camera system of the type having a detector head including a planar face, locations on said face being definable by x and y coordinates in the frame of reference of said face, the head being rotatable in a prescribed path about a longitudinal axis, wherein errors result from indigenous deviations in the rotational path of that head relative to the prescribed path, the steps comprising:
   (a) calibrating the system by measuring the indigenous deviations in the x and y direction of said planar face for a selected viewing angle and repeating such measurements for a plurality of a viewing angles until a pair of x and y shift values are calculated for each viewing angle of interest;
   (b) storing in a memory the x and y shift values for each of said viewing angles;
   (c) collecting emission data as said detector head is rotated about said longitudinal axis, each datum representative of a single scintillation event; and
   (d) correcting the location of each event detected at a given viewing angle by altering the location of detection in the x and y coordinate respectively by the x and y shift values stored in memory for said viewing angle.

2. The method according to claim 1 wherein the calibrating step for measuring the y shift values comprises collecting a point response function of the system at each viewing angle of interest.

3. The method according to claim 1 wherein the correcting step is accomplished in real time on an event-by-event basis.

4. The method according to claim 1 wherein the correction step is accomplished within the camera.

5. The method according to claim 1 wherein the prescribed path for rotation of the detector head is a circle of a preselected radius and the calibrating step is repeated a plurality of times, once for each circle of a different radius.

* * * * *